United States Patent
Voeste et al.

(10) Patent No.: US 8,546,304 B2
(45) Date of Patent: Oct. 1, 2013

(54) COMPOSITION AND METHOD FOR IMPROVING PLANT HEALTH

(75) Inventors: Dirk Voeste, Limburgerhof (DE); Martin P. Mascianica, Chapel Hill, NC (US); Hendrik Ypema, Cary, NC (US); Henry Van Tuyl Cotter, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/209,926

(22) Filed: Aug. 15, 2011

(65) Prior Publication Data

US 2011/0301029 A1    Dec. 8, 2011

Related U.S. Application Data

(63) Continuation of application No. 11/816,810, filed as application No. PCT/EP2006/060103 on Feb. 20, 2006.

(60) Provisional application No. 60/655,208, filed on Feb. 22, 2005.

(51) Int. Cl.
| | |
|---|---|
| A01C 1/06 | (2006.01) |
| A61K 31/44 | (2006.01) |
| A61K 31/4439 | (2006.01) |
| A01P 15/00 | (2006.01) |
| A01P 3/00 | (2006.01) |
| A01N 43/56 | (2006.01) |
| A01N 43/78 | (2006.01) |
| A01N 43/88 | (2006.01) |
| A01P 7/00 | (2006.01) |

(52) U.S. Cl.
USPC ............ 504/100; 504/130; 504/132; 504/139; 514/229.2; 514/341; 514/357; 514/365; 514/407

(58) Field of Classification Search
None
See application file for complete search history.

(56) References Cited

U.S. PATENT DOCUMENTS

| | | | |
|---|---|---|---|
| 3,060,084 | A | 10/1962 | Littler |
| 3,299,566 | A | 1/1967 | MacMullen |
| 3,920,442 | A | 11/1975 | Albert et al. |
| 4,144,050 | A | 3/1979 | Frensch et al. |
| 4,172,714 | A | 10/1979 | Albert |
| 5,013,659 | A | 5/1991 | Bedbrook et al. |
| 5,180,587 | A | 1/1993 | Moore |
| 5,208,030 | A | 5/1993 | Hoy et al. |
| 5,232,701 | A | 8/1993 | Ogawa et al. |
| 6,159,992 | A | 12/2000 | Müller et al. |
| 6,365,614 | B1 | 4/2002 | Schelberger et al. |
| 6,436,934 | B1 | 8/2002 | Schelberger et al. |
| 7,071,188 | B2 | 7/2006 | Watrin |
| 2005/0009703 | A1 | 1/2005 | Wachendorff-Neumann et al. |
| 2005/0148639 | A1 | 7/2005 | Ammermann et al. |
| 2007/0287720 | A1 | 12/2007 | Royalty et al. |
| 2008/0274882 | A1 | 11/2008 | Krohn et al. |

FOREIGN PATENT DOCUMENTS

| | | |
|---|---|---|
| EP | 0 142 924 | 5/1985 |
| EP | 0 193 259 | 9/1986 |
| EP | 0 242 236 | 10/1987 |
| EP | 0 242 246 | 10/1987 |
| EP | 0 257 993 | 3/1988 |
| EP | 0 376 279 | 7/1990 |
| GB | 2 095 558 | 10/1982 |
| WO | WO 91/13546 | 9/1991 |
| WO | WO 91/13972 | 9/1991 |
| WO | WO 91/19806 | 12/1991 |
| WO | WO 92/00377 | 1/1992 |
| WO | WO 92/11376 | 7/1992 |
| WO | WO 92/14827 | 9/1992 |
| WO | WO 95/01722 | 1/1995 |
| WO | WO 97/27189 | 7/1997 |
| WO | WO 98/08385 | 3/1998 |
| WO | WO 98/58544 | 12/1998 |
| WO | WO 99/31976 | 7/1999 |
| WO | WO 99/48366 | 9/1999 |
| WO | WO 99/63826 | 12/1999 |
| WO | WO 00/28825 | 5/2000 |
| WO | WO 00/30440 | 6/2000 |
| WO | WO 02/37964 | 5/2002 |
| WO | WO 02/102148 A2 | 12/2002 |
| WO | WO 03/015515 | 2/2003 |
| WO | WO 03/059067 | 7/2003 |
| WO | WO 03/090538 | 11/2003 |
| WO | WO 2005/000021 | * 1/2005 |
| WO | WO 2006/023899 | 3/2006 |
| WO | WO 2006/069654 | 7/2006 |

OTHER PUBLICATIONS

DW 1999-571928/48, Mar. 24, 1998, Eng. Abstract of WO 99/48366.
DW 2000-387563/33, Nov. 16, 1998, Eng. Abstract of WO 00/28825.
Pesticides Manual, 11$^{th}$ Ed. (1997), The British Crop Protection Council, London, p. 566-568.
Pesticides Manual, 11$^{th}$ Ed. (1997), The British Crop Protection Council, London, p. 792-794.
Pesticides Manual, 11$^{th}$ Ed. (1997), The British Crop Protection Council, London, p. 794-795.
Jayasena K.W.; Loughman R; Majewski J., Evaluation of fungicides in control of spot-type net blotch on barley: crop protection, vol. 21, Feb. 2002, pp. 63-69, XP 002347515.
Pesticides Manual, 13$^{th}$ Ed. (2003), The British Crop Protection Council, London, p. 7-8.
Pesticides Manual, 13$^{th}$ Ed. (2003), The British Crop Protection Council, London, p. 198-199.
Pesticides Manual, 13$^{th}$ Ed. (2003), The British Crop Protection Council, London, p. 336.

(Continued)

Primary Examiner — Kortney L Klinkel
(74) Attorney, Agent, or Firm — Brinks Hofer Gilson & Lione

(57) ABSTRACT

The present invention relates to plant-protecting active ingredient mixtures comprising, as active components, a neonicotinoid and one or two fungicides selected from pyraclostrobin and boscalid, in synergistically effective amounts and to a method of improving the health of plants by to the plants or the locus thereof by applying said mixtures.

22 Claims, No Drawings

(56) References Cited

OTHER PUBLICATIONS

Pesticides Manual, 13th Ed. (2003), The British Crop Protection Council, London, p. 562-564.
Pesticides Manual, 13th Ed. (2003), The British Crop Protection Council, London, p. 705-706.
Pesticides Manual, 13th Ed. (2003), The British Crop Protection Council, London, p. 958-959.
Pesticides Manual, 13th Ed. (2003), The British Crop Protection Council, London, p. 960-961.
Pesticides Manual, 13th Ed. (2003), The British Crop Protection Council, London, p. 842-843.
Pesticides Manual, 13th Ed. (2003), The British Crop Protection Council, London, p. 104.

* cited by examiner

US 8,546,304 B2

COMPOSITION AND METHOD FOR IMPROVING PLANT HEALTH

This application is a continuation of U.S. application Ser. No. 11/816,810, filed Aug. 21, 2007, which is a National Stage application of International Application No. PCT/EP2006/060103, filed Feb. 20, 2006, which claims the benefit of U.S. Provisional Application No. 60/655,208 filed Feb. 22, 2005, the entire contents of which are hereby incorporated herein by reference.

The present invention relates to plant-protecting active ingredient mixtures having synergistically enhanced action and to a method of improving the health of plants by applying said mixtures to the plants or the locus thereof.

One typical problem arising in the field of pest control lies in the need to reduce the dosage rates of the active ingredient in order to reduce or avoid unfavorable environmental or toxicological effects whilst still allowing effective pest and pathogen control.

Another problem encountered concerns the need to have available pest control agents which are effective against a broad spectrum of pests and pathogens.

Another problem underlying the present invention is the desire for compositions that improve plants, a process which is commonly and hereinafter referred to as "plant health". For example, advantageous properties that may be mentioned are improved crop characteristics including: emergence, crop yields, protein content, more developed root system (improved root growth), tillering increase, increase in plant height, bigger leaf blade, less dead basal leaves, stronger tillers, greener leaf color, pigment content, photosynthetic activity, less fertilizers needed, less seeds needed, more productive tillers, earlier flowering, early grain maturity, less plant verse (lodging), increased shoot growth, enhanced plant vigor, increased plant stand and early germination; or any other advantages familiar to a person skilled in the art.

Another difficulty in relation to the use of pesticides is that the repeated and exclusive application of an individual pesticidal compound leads in many cases to a rapid selection of pests or pathogens that have developed natural or adapted resistance against the active compound in question.

It was therefore an object of the present invention to provide pesticidal mixtures which solve the problems outlined above.

The combating of harmful phytopathogenic fungi is not the only problem the farmer has to face. Also harmful insects and other pestscan cause a great damage to crops and other plants. An efficient combination of fungicidal and insecticidal activity is desirable to overcome this problem. Thus, it is a further object of the present invention to provide a mixture that, on the one hand, has good fungicidal activity, and, on the other hand, good insecticidal activity, resulting in a broader pesticidal spectrum of action.

We have found that this object is in part or in whole achieved by the combination of active compounds defined at the outset.

Especially, it has been found that a mixture of a neonicotinoid, preferably acetamiprid, clothianidin, dinotefuran, imidacloprid, nitenpyram, thiacloprid or thiamethoxam, more preferably acetamiprid, clothianidin, imidacloprid or thiamethoxam most preferably thiamethoxam and one or two fungicides selected from pyraclostrobin and boscalid achieves and mixtures comprising boscalid and metalaxyl show markedly enhanced action against plant pathogens compared to the control rates that are possible with the individual compounds and/or is suitable for improving the health of plants when applied to plants, parts of plants, seeds, or at their locus of growth. Mixtures of thiamethoxam with certain strobilurine fungicides are known from WO99/48366. However, all of the strobilurines mentioned in that document are acetic acid derivatives, whereas pyraclostrobin of the present invention is a methyl carbamate.

WO02/102148 discloses mixtures of fludioxonil, metalaxyl and a strobilurine fungicide which optionally may further contain an insecticide, inter alia thiamethoxam. The strobilurine fungicides disclosed all are acetic acid derivatives.

In WO 00/28825, at least quaternary compositions are described that comprise an insecticide such as thiamethoxam and three fungicides selected from acylalanines, for example metalaxyl, phenylpyrroles, for example fludioxonil, and triazoles, for example difenoconazole. Preferred is a composition comprising thiamethoxam, mefenoxam, fludioxonil and difenoconazole.

None of this documents mentions mixtures of thiamethoxam with pyraclostrobin or boscalid or mixtures comprising boscalid and metalaxyl.

Acetamiprid is an insecticide. See, for example, the Pesticide Manual, 13th Ed. (2003), The British Crop Protection Council, London, page 7.

Clothianidin is an insecticide. See, for example, the Pesticide Manual, 13th Ed. (2003), The British Crop Protection Council, London, page 198.

Dinotefuran is an insecticide. See, for example, the Pesticide Manual, 13th Ed. (2003), The British Crop Protection Council, London, page 336.

Imidacloprid is an insecticide. See, for example, the Pesticide Manual, 13th Ed. (2003), The British Crop Protection Council, London, page 562.

Nitenpyram is an insecticide. See, for example, the Pesticide Manual, 13th Ed. (2003), The British Crop Protection Council, London, page 705.

Thiacloprid is an insecticide. See, for example, the Pesticide Manual, 13th Ed. (2003), The British Crop Protection Council, London, page 958.

Thiamethoxam is an insecticide. See, for example, the Pesticide Manual, 13th Ed. (2003), The British Crop Protection Council, London, page 960.

Pyraclostrobin is a fungicide. See, for example, the Pesticide Manual, 13th Ed. (2003), The British Crop Protection Council, London, page 842.

Boscalid is a fungicide. See, for example, the Pesticide Manual, 13th Ed. (2003), The British Crop Protection Council, London, page 104.

Fludioxonil is a fungicide. See, for example, the Pesticide Manual, 11th Ed. (1997), The British Crop Protection Council, London, page 566.

Metalaxyl is a fungicide including: metalaxyl; metalaxyl consisting of more than 70% by weight of the R-enantiomer; metalaxyl consisting of more than 85% by weight of the R-enantiomer; metalaxyl consisting of more than 92% by weight of the R-enantiomer; metalaxyl consisting of more than 97% by weight of the R-enantiomer; and mefenoxam (i.e., R-metalaxyl or metalaxyl-M) wherein the metalaxyl component is pure R-metalaxyl which is substantially free of S-enantiomer. See, for example, the Pesticide Manual, 11th Ed. (1997), The British Crop Protection Council, London, page 792; and the Pesticide Manual, 11th Ed. (1997), The British Crop Protection Council, London, page 794. Preferably, the term metalaxyl as used herein refers to mefenoxam.

Preferred are mixtures comprising a neonicotinoid and pyraclostrobin, preferably
acetamiprid and pyraclostrobin,
clothianidin and pyraclostrobin,
dinotefuran and pyraclostrobin, imidacloprid and pyraclostrobin,
nitenpyram and pyraclostrobin,
thiacloprid and pyraclostrobin,
or thiamethoxam and pyraclostrobin, more preferably mixtures comprising
acetamiprid and pyraclostrobin,
clothianidin and pyraclostrobin,
imidacloprid and pyraclostrobin, or
thiamethoxam and pyraclostrobin, wherein most preferred are mixtures comprising
thiamethoxam and pyraclostrobin.

Preferred are furthermore mixtures comprising a neonicotinoid and boscalid, preferably
acetamiprid and boscalid,
clothianidin and boscalid,
dinotefuran and boscalid,
imidacloprid and boscalid,
nitenpyram and boscalid,
thiacloprid and boscalid,
or thiamethoxam and boscalid, more preferably mixtures comprising acetamiprid and boscalid,
clothianidin and boscalid,
imidacloprid and boscalid, or
thiamethoxam and boscalid, wherein mixtures comprising thiamethoxam and boscalid are most preferred.

Another preferred embodiment of the present invention comprises mixtures comprising
a neonicotinoid, pyraclostrobin and boscalid, preferably
acetamiprid, pyraclostrobin and boscalid,
clothianidin, pyraclostrobin and boscalid,
dinotefuran, pyraclostrobin and boscalid,
imidacloprid, pyraclostrobin and boscalid,
nitenpyram, pyraclostrobin and boscalid,
thiacloprid, pyraclostrobin and boscalid,
or thiamethoxam, pyraclostrobin and boscalid, more preferably mixtures comprising acetamiprid, pyraclostrobin and boscalid,
clothianidin, pyraclostrobin and boscalid,
imidacloprid, pyraclostrobin and boscalid, or
thiamethoxam, pyraclostrobin and boscalid, wherein most preferred are mixtures comprising thiamethoxam, pyraclostrobin and boscalid.

The mixtures of the present invention may further comprise metalaxyl.

Accordingly, preferred mixtures comprise a neonicotinoid, pyraclostrobin and metalaxyl, preferably
acetamiprid, pyraclostrobin and metalaxyl,
clothianidin, pyraclostrobin and metalaxyl,
dinotefuran, pyraclostrobin and metalaxyl,
imidacloprid, pyraclostrobin and metalaxyl,
nitenpyram, pyraclostrobin and metalaxyl,
thiacloprid, pyraclostrobin and metalaxyl,
or thiamethoxam, pyraclostrobin and metalaxyl, more preferably mixtures comprising acetamiprid, pyraclostrobin and metalaxyl,
clothianidin, pyraclostrobin and metalaxyl,
imidacloprid, pyraclostrobin and metalaxyl, or
thiamethoxam, pyraclostrobin and metalaxyl, wherein most preferred are mixtures comprising thiamethoxam, pyraclostrobin and metalaxyl.

Furthermore, preferred mixtures comprise a neonicotinoid, boscalid and metalaxyl, preferably
acetamiprid, boscalid and metalaxyl,
clothianidin, boscalid and metalaxyl,
dinotefuran, boscalid and metalaxyl,
imidacloprid, boscalid and metalaxyl,
nitenpyram, boscalid and metalaxyl,
thiacloprid, boscalid and metalaxyl,
or thiamethoxam, boscalid and metalaxyl, more preferably mixtures comprising acetamiprid, boscalid and metalaxyl,
clothianidin, boscalid and metalaxyl,
imidacloprid, boscalid and metalaxyl, or
thiamethoxam, boscalid and metalaxyl, wherein most preferred are mixtures comprising thiamethoxam, boscalid and metalaxyl are preferred.

In another preferred embodiment of the present invention, preferred mixtures comprise
a neonicotinoid, pyraclostrobin, boscalid, and metalaxyl, preferably
acetamiprid, boscalid, pyraclostrobin and metalaxyl,
clothianidin, boscalid, pyraclostrobin and metalaxyl,
dinotefuran, boscalid, pyraclostrobin and metalaxyl,
imidacloprid, boscalid, pyraclostrobin and metalaxyl,
nitenpyram, boscalid, pyraclostrobin and metalaxyl,
thiacloprid, boscalid, pyraclostrobin and metalaxyl,
or thiamethoxam, boscalid, pyraclostrobin and metalaxyl, more preferrably mixtures comprising
acetamiprid, boscalid, pyraclostrobin and metalaxyl,
clothianidin, boscalid, pyraclostrobin and metalaxyl,
imidacloprid, boscalid, pyraclostrobin and metalaxyl, or
thiamethoxam, boscalid, pyraclostrobin and metalaxyl, wherein most preferred are mixtures comprising thiamethoxam, pyraclostrobin, boscalid and metalaxyl.

Another preferred embodiment of the present invention comprises mixtures comprising boscalid and metalaxyl All embodiments of the above-mentioned mixtures are herein below also referred to as "inventive mixtures" or "mixtures according to the invention".

The inventive mixtures are suitable for foliar application in living crops of plants as well as, in particular, for dressing applications on plant propagation material. The latter term embraces seeds of all kinds (fruit, tubers, grains), cuttings, cut shoots and the like. One particular field of application is the treatment of all kinds of seeds.

In addition to the mixtures, this invention also relates to a method of controlling fungi and/or improving the health of plants, which comprises treating a site, for example a plant or a plant propagation material, that is infested or liable to be infested by fungi with a) a neonicotinoid, preferably acetamiprid, clothianidin, dinotefuran, imidacloprid, nitenpyram, thiacloprid or thiamethoxam, more preferably acetamiprid, clothianidin, imidacloprid or thiamethoxam most preferably thiamethoxam, with b) pyraclostrobin, and/or with c) boscalid, in any desired sequence or simultaneously, that is, jointly or separately.

In addition, the invention furthermore relates to a method of controlling fungi and/or improving the health of plants, which comprises treating a site, for example a plant or a plant propagation material, that is infested or liable to be infested by fungi with a) boscalid and b) metalaxyl, in any desired sequence or simultaneously, that is, jointly or separately.

Generally, the invention furthermore relates to a method of controlling fungi and/or improving the health of plants, which comprises treating a site, for example a plant or a plant propagation material, that is infested or liable to be infested by fungi with the pesticides present in a inventive mixture in any desired sequence or simultaneously, that is, jointly or separately.

Advantageous mixing ratios by weight of the active ingredients are neonicotinoid, preferably acetamiprid, clothianidin, dinotefuran, imidacloprid, nitenpyram, thiacloprid or thiamethoxam, more preferably acetamiprid, clothianidin, imidacloprid or thiamethoxam most preferably thiamethoxam:pyraclostrobin or :boscalid from 100:1 to 1:100. A preferred ratio for neonicotinoid, preferably acetamiprid, clothianidin, dinotefuran, imidacloprid, nitenpyram, thiacloprid or thiamethoxam, more preferably acetamiprid, clothianidin, imidacloprid or thiamethoxam most preferably thiamethoxam:boscalid is 10:1 to 1:10. For example, for seed treatment, ratios of 3 kg:30 g a.i./100 kg, 100 g:1 g a.i./100 kg, 30 g:3 kg a.i./100 kg or 1 g:100 g a.i./100 kg of seed are suitable. For some specific crop seeds, such as lettuce or onions, the rates can be higher.

Furthermore, advantageous mixing ratios by weight of three active ingredients are thiamethoxam:pyraclostrobin:boscalid in which each combination of two ingredients in the mixture of three ingredients ranges from 100:1 to 1:100. The amount of any one of the ingredients in the mixture may range from 1 g to 3 kg a.i./100 kg of seed. For example, ratios of 50 g:5 g:20 g a.i./100 kg is suitable.

Advantageously, the pesticidal mixtures may comprise metalaxyl in which each combination of two ingredients in the mixture of two to four ingredients ranges from 100:1 to 1:100.

Advantageous mixing ratios by weight of the active ingredients are metalaxyl:boscalid from 100:1 to 1:100 by weight.

The novel active ingredient mixtures have very advantageous curative, preventive and systemic fungicidal properties for protecting cultivated plants. As has been mentioned, said active ingredient mixtures can be used to inhibit or destroy the pathogens that occur on plants or parts of plants (fruit, blossoms, leaves, stems, tubers, roots) of different crops or useful plants, while at the same time those parts of plants which grow later are also protected from attack by such pathogens. Active ingredient mixtures have the special advantage of being highly active against diseases in the soil that mostly occur in the early stages of plant development.

Specifically, they are suitable for controlling the following harmful fungi:
  *Alternaria* species on vegetables and fruit,
  *Bipolaris* and *Drechslera* species on cereals, rice and turf,
  *Blumeria graminis* (powdery mildew) on cereals,
  *Botrytis cinerea* (gray mold) on strawberries, vegetables, ornamentals and grapevines,
  *Didymella* species on various plants,
  *Erysiphe cichoracearum* and *Sphaerotheca fuliginea* on cucurbits,
  *Fusarium* and *Verticillium* species on various plants,
  *Mycosphaerella* species on cereals, bananas and peanuts,
  *Phakopsara pachyrhizi* and *Phakopsara meibomiae* on soybeans
  *Phytophthora* species on various plants,
  *Plasmopara viticola* on grapevines,
  *Podosphaera leucotricha* on apples,
  *Pseudocercosporella herpotrichoides* on wheat and barley,
  *Pseudoperonospora* species on hops and cucumbers,
  *Puccinia* species on cereals,
  *Pyricularia oryzae* on rice,
  *Pythium* species on various plants,
  *Rhizoctonia* species on cotton, legumes, rice and turf,
  *Sclerotinia* species on various plants,
  *Septoria tritici* and *Stagonospora nodorum* on wheat,
  *Thielaviopsis* species on various plants,
  *Uncinula necator* on grapevines,
  *Ustilago* species on cereals and sugar cane, and
  *Venturia* species (scab) on apples and pears.

The mixtures, which comprise a neonicotinoid are also suitable for controlling the following harmful insects from the order of the
lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absolute, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*,
beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcate, Ceuthorrhynchus assimilis, Ceuthorrhynchus napi, Chaetocnema tibialis, Conoderus vespertinus, Crioceris asparagi, Diabrotica longicornis, Diabrotica speciosa, Diabrotica 12-punctata, Diabrotica virgifera, Diloboderus abderus, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Oryazophagus oryzae, Otiorrhynchus ovatus, Phaedon cochleariae, Phyllotreta chrysocephala, Phyllophaga* sp., *Phyllophaga cuyabana, Phyllophaga triticophaga, Phyllopertha horticola, Phyllotreta nemorum, Phyllotreta striolata, Popillia japonica, Sitona lineatus* and *Sitophilus granaria,*
dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucille caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa,*
thrips (Thysanoptera), e.g. *Frankliniella fusca, Frankliniella occidentalis, Frankliniella tritici, Scirtothrips citri, Thrips oryzae, Thrips palmi* and *Thrips tabaci,* hymenopterans (Hymenoptera), e.g. *Acromyrmex ambuguus, Acromyrmex crassispinus, Acromyrmex heiery, Acromyrmex landolti, Acromyrmex subterraneus, Athalia rosae, Atta capiguara, Atta cephalotes, Atta laevigata, Atta robusta, Atta sexdens, Atta texana, Hoplocampa minuta, Hoplocampa testudinea, Monomorium pharaonis, Solenopsis geminate* and *Solenopsis invicta*, heteropterans (Heteroptera), e.g. *Acrosternum hilare, Blissus leucopterus, Cyrtopeltis notatus, Dichelops furcatus, Dysdercus cingulatus, Dysdercus intermedius, Euchistos heros, Eurygaster integriceps, Euschistus impictiventris, Leptoglossus phyllopus, Lygus lineolaris, Lygus pratensis, Nezara viridula, Piesma quadrata, Piezodorus guildini, Solubea insularis* and *Thyanta perditor,*

Hemiptera and Homoptera, e.g. *Acrosternum hilare, Blissus leucopterus, Cyrtopeltis notatus, Diaphorina citri, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus,* termites (Isoptera), e.g. *Calotermes flavicollis, Cornitermes cumulans, Heterotermes tenuis, Leucotermes flavipes, Neocapritemes opacus, Procornitermes triacifer; Reticulitermes lucifugus, Syntermes molestus,* and *Termes natalensis,* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus,*

Arachnoidea, such as arachnids, e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei*, and Eriophyidae spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;* thrips (Thysanoptera), e.g. *Frankliniella fusca, Frankliniella occidentalis, Frankliniella schultzei, Frankliniella tritici, Scirtothrips citri, Thrips oryzae, Thrips palmi* and *Thrips tabaci.*

In particular, the inventive mixtures are suitable for combating pests of the orders Coleoptera, Lepidoptera, Thysanoptera, Homoptera, Isoptera, and Orthoptera.

They are also suitable for controlling the following plant parasitic nematodes such as *Meloidogyne, Globodera, Heterodera, Radopholus, Rotylenchulus, Pratylenchus* and other genera.

Suitable targets for seed treatment are various crop seeds, fruit species, vegetables, spices and ornamental seed, for example corn/maize (sweet and field), durum wheat, soybean, wheat, barley, oats, rye, triticale, bananas, rice, cotton, sunflower, potatoes, pasture, alfalfa, grasses, turf, sorghum, rapeseed, *Brassica* spp., sugar beet, egg-plants, tomato, lettuce, iceberg lettuce, pepper, cucumber, squash, melon, bean, dry-beans, peas, leek, garlic, onion, cabbage, carrot, tuber such as sugar cane, tobacco, coffee, turf and forage, cruciferous, cucurbits, grapevines, pepper, fodder beet, oil seed rape, pansy, impatiens, petunia and geranium.

The term seed treatment comprises all suitable seed treatment techniques known in the art, such as, but not limited to, seed dressing, seed coating, seed dusting, seed soaking, seed film coating, seed multilayer coating, seed encrusting, seed dripping, and seed pelleting.

The active ingredient mixtures according to the invention are especially advantageous for seed treatment of oil seed rape, wheat, corn, rye, barley, oats, sorghum, sunflowers, rice, maize, turf and forage, sugar beet, beans, peas, soybeans, ornamentals, and vegetables such as cucurbits, tomatoes, eggplant, potatoes, pepper, lettuce, cabbage, carrots, cruciferous.

Especially preferred is the seed treatment of oil seed rape, wheat, beans, corn, soybeans, sugar beet, rice, vegetables, and ornamentals.

The mixtures according to the invention are most preferably used for the seed treatment of oil seed rape.

In addition, mixtures according to the invention may also be used in crops which tolerate the action of herbicides or fungicides or insecticides owing to breeding, including genetic engineering methods.

For example, mixtures according to the invention can be employed in transgenic crops which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, mixtures according to the invention can be used also for the treatment of plants which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

In addition, the synergistically enhanced action of the mixtures manifests itself, for example, in lower rates of application and/or in a longer duration of action and/or higher crop yields. Such enhancements were not to be expected from the sum of the actions of the individual components.

It has been found that the action of the inventive mixtures, e.g. of the mixture of a neonicotinoid, preferably acetamiprid, clothianidin, dinotefuran, imidacloprid, nitenpyram, thiacloprid or thiamethoxam, more preferably acetamiprid, clothianidin, imidacloprid or thiamethoxam most preferably thiamethoxam with pyraclostrobin and/or boscalid goes far beyond the fungicidal action of the fungicide(s) present in the mixture alone. It has been shown that the mixtures exhibit plant health effects (as outlined above) in the frame of the present invention. The term plant health comprises various sorts of improvements of plants that are not connected to the control of pests with the said mixture of a neonicotinoid, preferably acetamiprid, clothianidin, dinotefuran, imidacloprid, nitenpyram, thiacloprid or thiamethoxam, more preferably acetamiprid, clothianidin, imidacloprid or thiamethoxam most preferably thiamethoxam with pyraclostrobin and/or boscalid.

The active ingredient mixtures can be used in the form of premix formulations or the active ingredients can be applied to the area, plant or seed to be treated simultaneously or in immediate succession, if desired together with further carriers, surfactants or other application-promoting adjuvants customarily employed in formulation technology.

The formulations are prepared in a known manner, for example by extending the active compound with auxiliaries suitable for the formulation of agrochemicals, such as solvents and/or carriers, if desired surfactants (e.g. surfactants, adjuvans and/or dispersants), preservatives, antifoaming agents, anti-freezing agents, for seed treatment formulation also optionally colorants and/or binders and/or gelling agents. (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8).

Solvents/auxiliaries which are suitable include:
water, aromatic solvents (for example Solvesso products, xylene), paraffins (for example mineral fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.
carriers such as ground natural minerals (for example kaolins, clays, talc, chalk) and ground synthetic minerals (for example highly disperse silica, silicates); emulsifiers such as nonionic and anionic emulsifiers (for example polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Seed Treatment formulations may additionally comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®)

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. The active compounds are employed in a purity of from 90% to 100%, preferably 95% to 100% (according to NMR spectrum). The following are examples of formulations: 1. Products for dilution with water for foliar application/for seed treatment purposes, these products can be applied diluted or undiluted.

A) Soluble Concentrates (SL, LS)

10 parts by weight of the active compounds are dissolved in water or in a water-soluble solvent. As an alternative, wetters or other auxiliaries are added. The active compound dissolves upon dilution with water.

B) Dispersible Concentrates (DC)

20 parts by weight of the active compounds are dissolved in cyclohexanone with addition of a dispersant, for example polyvinylpyrrolidone. Dilution with water gives a dispersion.

C) Emulsifiable Concentrates (EC)

15 parts by weight of the active compounds are dissolved in xylene with addition of calcium dodecylbenzenesulfonate and castor oil ethoxylate (in each case 5% strength). Dilution with water gives an emulsion.

D) Emulsions (EW, EO, ES)

40 parts by weight of the active compounds are dissolved in xylene with addition of calcium dodecylbenzenesulfonate and castor oil ethoxylate (in each case 5% strength). This mixture is introduced into water by means of an emulsifier (Ultraturax) and made into a homogeneous emulsion. Dilution with water gives an emulsion.

E) Suspensions (SC, OD, FS)

In an agitated ball mill, 20 parts by weight of the active compounds are comminuted with addition of dispersant, wetters and water or an organic solvent to give a fine active compound suspension. Dilution with water gives a stable suspension of the active compound.

F) Water-Dispersible Granules and Water-Soluble Granules (WG, SG)

50 parts by weight of the active compounds are ground finely with addition of dispersants and wetters and made into water-dispersible or water-soluble granules by means of technical appliances (for example extrusion, spray tower, fluidized bed). Dilution with water gives a stable dispersion or solution of the active compound.

G) Water-Dispersible Powders and Water-Soluble Powders (WP, SP, WS)

75 parts by weight of the active compounds are ground in a rotor-stator mill with addition of dispersant, wetters and silica gel. Dilution with water gives a stable dispersion or solution with the active compound.

2. Products to be applied undiluted for foliar application. For seed treatment purposes, these products can be applied diluted or undiluted.

H) Dustable Powders (DP, DS)

5 parts by weight of the active compounds are ground finely and mixed intimately with 95% of finely divided kaolin. This gives a dustable product.

I) Granules (GR, FG, GG, MG)

0.5 part by weight of the active compounds is ground finely and associated with 95.5% carriers. Current methods are extrusion, spray-drying or the fluidized bed. This gives granules to be applied undiluted.

J) ULV Solutions (UL)

10 parts by weight of the active compounds are dissolved in an organic solvent, for example xylene. This gives a product to be applied undiluted.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; it is intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

Various types of oils, wetters, adjuvants, herbicides, fungicides, other pesticides, or bactericides may be added to the active compounds, if appropriate just immediately prior to use (tank mix). These agents can be admixed with the agents according to the invention in a weight ratio of 1:10 to 10:1.

The agrochemical compositions usually comprise 0.1 to 99%, preferably 0.1 to 95%, of active ingredients, 99.9 to 1%, preferably 99.9 to 5%, of a solid or liquid adjuvant, and 0 to 25%, preferably 0.1 to 25%, of a surfactant.

Depending on the desired effect, the application rates of the mixtures according to the invention are from 0.1 g/ha to 2000 g/ha, preferably from 50 to 1500 g/ha, in particular from 50 to 750 g/ha.

In the treatment of seed, the application rates of the mixture are generally from 0.1 g to 5 kg per 100 kg of seed, preferably from 1 g to 2.5 kg per 100 kg of seed, in particular from 1 g to 1 kg per 100 kg of seed.

In the control or pests, the separate or joint application of the inventive mixtures or compositions comprising them is carried out by spraying or dusting or otherwise applying the mixture to the seeds, the seedlings, the plants or the soils before or after sowing of the plants or before or after emergence of the plants.

Conventional seed treatment formulations include for example flowable concentrates FS, solutions LS, powders for dry treatment DS, water dispersible powders for slurry treatment WS, water-soluble powders SS and emulsion ES and EC, wherein FS and WS are the most preferred ones.

In accordance with one variant, a further subject of the invention is a method of treating soil by the application, in particular into the seed drill: either of a granular formulation containing the two active ingredients in combination or as a composition, or of a mixture of two granular formulations, each containing one of the two active ingredients, with optionally one or more solid or liquid, agriculturally acceptable carriers and/or optionally with one or more agriculturally acceptable surfactants. This method is advantageously employed in seedbeds of cereal, maize, cotton and sunflower.

The invention also relates to the propagation products of plants, and especially the seed comprising, that is treated with a mixture as defined above or a composition containing the inventive mixture or a mixture of compositions each providing one of the active ingredients.

The seed comprises the inventive mixtures in an amount of from 0.1 g to 5 kg per 100 kg of seed.

The synergistic pesticidal action of the inventive mixtures can be demonstrated by the experiments below:

Treatments

Each mixture partner is evaluated separately at the same rates as used in the mixtures. Synergism is determined by comparing the expected biological effect on plant health or on disease control from the mixture based on the individual effects from the separate partners to the biological effect seen with the mixture. Abbott's formula can be used to make this comparison.

Seed Treatment—Cotton

Compounds are used as technical materials and formulated in 15% acetone in 0.05% aqueous Tween 20® (Polyoxyethylene sorbitan monolaureate). Fifty cotton seeds are placed in a 120 ml glass vial and 300 µl of the compound preparation are pipetted onto the side of the vial just above the seeds. The vial can shaken for 3 minutes and the treated seeds were placed on aluminum foil to dry.

Plant Health 24 cotton seeds of each treatment are planted, 2 seeds per 7.5 cm square plastic pot containing Metro Mix 360 planting material and maintained in the greenhouse. Measurements taken of plant health are time to emergence, percent emergence, shoot biomass and root biomass at the 2-true-leaf stage.

Synergistic Plant Disease Control

To determine treatment effects on plant disease control, 12 cotton seeds of each treatment are planted, 2 seeds per 7.5 cm square plastic pot containing sandy soil and challenged with fungal pathogens. Two fungal pathogens can be used: *Pythium* sp. and *Rhizoctonia* sp. Plants are maintained in the greenhouse with bottom watering. Measurements of the severity of damping off and root rot are taken and then percent disease control is calculated for each treatment based on the untreated controls.

The test results will show that the mixtures according to the invention show a considerable enhanced activity demonstrating synergism compared to the calculated sum of the single activities.

Synergistic Plant Health Effects

The synergistic plant health effects of the inventive mixtures has been demonstrated by the experiments described below:

To determine seed treatment effects of the inventive mixtures on plant health soft red winter wheat seeds (Variety Coker 9663) were treated with mixtures and with each mixture partner separately. Compounds were applied in water if formulated or in 25% acetone if technical material. For mixtures, water was used as the carrier unless one or more partners was used as technical material then 25% acetone was used as the carrier. Each treatment was prepared in a 20 ml glass vial. Then 25 seeds were added, and the vial was vortexed for one minute. After treatment, seeds were allowed to dry.

Plant growth pouches (18 cm×16.5 cm Cyg™ Germination Pouches, Mega-International) were watered with 17-20 ml water, and 4 seeds were placed in each growth pouch on the same day as treatment. Replication was 4× to 5×. Growth pouches were incubated at 25 C with 14 hours light and watered as needed. Germination was evaluated at 3-4 and 7-8 days after treatment (DAT). Root length and wet weight mass and shoot length and wet weight mass were evaluated 7-8 DAT.

Expected responses from the mixture were calculated based on the responses observed when each mixture partner was applied alone.

Percent effects for each of the mixture partners (MP1 and MP2) applied solo were calculated as follows:

MP1=(Control response−MP1 response)/Control response*100%

MP2=(Control response−MP2 response)/Control response*100%

The appropriate control response was used for each mixture partner.

Then, the expected % response for the mixture was calculated using Abbott's formula as follows:

$E$ % response=(MP1+MP2)−(MP1*MP2)/100

Finally, the expected response for the mixture was calculated by applying the expected % response to the appropriate control for the mixture, which is the solvent blank control, as follows:

Expected response=Control response−(Control response*$E$ % response/100)

EXPERIMENT 1

For each of the four measures of wheat plant health (root length, root mass, shoot length, and shoot mass), the actual response observed for the thiamethoxam plus boscalid mixture (50 g ai+20 g ai respectively per 100 kg seed) was greater than the expected response based on the responses observed when each partner was applied alone demonstrating a synergistic effect on plant health. (Table 1).

Percent germination of the wheat seeds for all treatments was 100%.

TABLE 1

| | Thiamethoxam + Boscalid (50 + 20 g ai/100 kg seed) | |
| --- | --- | --- |
| Wheat Plant Growth Measurement | Expected Mixture Response based on Median Solo Effects | Actual Mixture Response |
| Root Length (cm) | 14.9 | 15.5 |
| Root Mass (g) | 0.044 | 0.070 |
| Shoot Length (cm) | 14.3 | 15.8 |
| Shoot Mass (g) | 0.063 | 0.067 |

Evaluations were conducted on 20 seedlings per treatment, 5 reps with 4 seedlings each.

EXPERIMENT 2

For three of the four measures of wheat plant health (root mass, shoot length, shoot mass), the actual response observed for the thiamethoxam and metalaxyl mixture (50 g ai+20 g ai respectively per 100 kg seed) was greater than the expected response based on the responses observed when each partner was applied alone (Table 2).

Percent germination of the wheat seeds for all treatments was 100%.

Evaluations were conducted on 16 seedlings per treatment, 4 reps with 4 seedlings each.

TABLE 2

| Wheat Plant Growth Measurement" | Thiamethoxam + Metalaxyl (50 + 20 g ai/100 kg seed | |
|---|---|---|
| | Expected Mixture Response based on Median Solo Effects | Actual Mixture Response |
| Root Length (cm) | 15.8 | 15.0 |
| Root Mass (g) | 0.057 | 0.066 |
| Shoot Length (cm) | 13.6 | 16.1 |
| Shoot Mass (g) | 0.054 | 0.062 |

Evaluations were conducted on 16 seedlings per treatment, 4 reps with 4 seedlings each.

The invention claimed is:

1. A pesticidal mixture comprising, as active components, a neonicotinoid, pyraclostrobin and metalaxyl, in synergistically effective amounts.

2. The pesticidal mixture according to claim 1, in which each combination of two ingredients in the mixture of three ingredients ranges from 100:1 to 1:100.

3. The pesticidal mixture according to claim 1, wherein the neonicotinoid is thiamethoxam.

4. The pesticidal mixture according to claim 1, wherein the neonicotinoid is clothianidin.

5. The pesticidal mixture according to claim 1, wherein the neonicotinoid is imidacloprid.

6. The pesticidal mixture according to claim 1, wherein the neonicotinoid is acetamiprid.

7. A method of improving the health of plants, which comprises applying in any desired sequence, including simultaneously, separately, in succession, or as a mixture, a synergistically effective amount of a neonicotinoid, pyraclostrobin and metalaxyl.

8. The method as claimed in claim 7, wherein the amount of the neonicotinoid, pyraclostrobin and metalaxyl or the mixture thereof applied is from 0.1 g/ha to 2000 g/ha.

9. The method of claim 7, in which each combination of two ingredients in the mixture of three ingredients ranges from 100:1 to 1:100.

10. The method of claim 8, wherein the neonicotinoid is thiamethoxam, clothianidin, imidacloprid, or acetamiprid.

11. A method of controlling or preventing fungal infestation in plants, parts of plants, seeds, or at their locus of growth, which comprises applying in any desired sequence, including simultaneously, separately, succession, or as a mixture, a synergistically effective amount of a neonicotinoid, pyraclostrobin and metalaxyl.

12. The method as claimed in claim 1, wherein the amount of the neonicotinoid, pyraclostrobin and metalaxyl or the mixture thereof applied is from 0.1 g/ha to 2000 g/ha.

13. The method of claim 12, in which each combination of two ingredients in the mixture of three ingredients ranges from 100:1 to 1:100.

14. The method of claim 12, wherein the neonicotinoid is thiamethoxam, clothianidin, imidacloprid, or acetamiprid.

15. A method of protection of seeds comprising contacting the seeds before sowing and/or after pregermination with a mixture as defined in claim 1 in synergistically effective amounts.

16. The method of claim 15, wherein the mixture is applied in an amount from 0.1 g/ha to 2000 g/ha.

17. The method of claim 16, in which each combination of two ingredients in the mixture of three ingredients ranges from 100:1 to 1:100.

18. The method of claim 16, wherein the neonicotinoid is thiamethoxam, clothianidin, imidacloprid, or acetamiprid.

19. A plant propagation material treated with the mixtures of claim 1 in an amount of from 0.1 g to 5 kg per 100 kg of seeds.

20. The plant propagation material of claim 19, wherein the propagation material is seeds.

21. The propagation material of claim 19, in which each combination of two ingredients in the mixture of three ingredients ranges from 100:1 to 1:100.

22. The propagation material of claim 20, wherein the neonicotinoid is thiamethoxam, clothianidin, imidacloprid, or acetamiprid.

* * * * *

UNITED STATES PATENT AND TRADEMARK OFFICE
CERTIFICATE OF CORRECTION

| | | |
|---|---|---|
| PATENT NO. | : 8,546,304 B2 | Page 1 of 1 |
| APPLICATION NO. | : 13/209926 | |
| DATED | : October 1, 2013 | |
| INVENTOR(S) | : Dirk Voeste et al. | |

It is certified that error appears in the above-identified patent and that said Letters Patent is hereby corrected as shown below:

In the Claims:

Claim 11, col. 16, line 6, before "succession" insert --in--.

Signed and Sealed this
Twenty-eighth Day of January, 2014

Michelle K. Lee
*Deputy Director of the United States Patent and Trademark Office*